United States Patent [19]
Barth

[11] 3,968,213
[45] July 6, 1976

[54] METHOD OF PREVENTING ASTHMATIC SYMPTOMS

[75] Inventor: Wayne E. Barth, East Lyme, Conn.

[73] Assignee: Pfizer Inc., New York, N.Y.

[22] Filed: Jan. 14, 1975

[21] Appl. No.: 541,017

Related U.S. Application Data

[62] Division of Ser. No. 299,871, Oct. 24, 1972, Pat. No. 3,883,653.

[52] U.S. Cl. .............................................. 424/251
[51] Int. Cl.² ...................................... A61K 31/505
[58] Field of Search .................................... 424/251

[56] References Cited
UNITED STATES PATENTS

| | | | |
|---|---|---|---|
| 3,745,161 | 7/1973 | Shen et al. | 424/250 |
| 3,864,493 | 2/1975 | Cairns et al. | 424/283 |
| 3,879,544 | 4/1975 | Reisner et al. | 424/337 |
| 3,883,653 | 5/1975 | Barth | 424/251 |
| 3,885,038 | 5/1975 | Pfister et al. | 424/283 |

Primary Examiner—Norman A. Drezin
Attorney, Agent, or Firm—Connolly and Hutz

[57] ABSTRACT

5-Carboxypyrimidine derivatives and their pharmaceutically acceptable basic salts, and their use as antiallergy agents.

3 Claims, No Drawings

METHOD OF PREVENTING ASTHMATIC SYMPTOMS

CROSS-REFERENCE TO RELATED APPLICATION

This application is a division of application Ser. No. 299,871 filed Oct. 24, 1972, and now U.S. Pat. No. 3,883,653.

BACKGROUND OF THE INVENTION

This invention relates to 5-carboxypyrimidines, and in particular to a series of bis(4-hydroxy-5-carboxy-2-pyrimidinyl)phenoxy alkanes and 2-substituted-4-hydroxy-5-carboxypyrimidines and their use as inhibitors of allergic reactions, and in particular allergic asthma.

Allergic reactions, the symptoms resulting from an antigen-antibody interaction, manifest themselves in a wide variety of ways and diffusely different organs and tissues. Among one of the most disabling and debilitating of these allergic reactions is asthma, characterized by episodes of breathlessness and wheezing.

Efforts to discover medicinal agents to alleviate the symptoms of this abnormal physiologic state have been extensive. As early as 1910, Matthews, *Brit. Med. J.*, 1, 441 (1910) reported the bronchodilator effects of epinephrine. Since then, Chen and Schmidt, *J. Pharmacol. Exper. Therap.*, 24,339 (1924), reported the use of the alkaloid ephedrine as an oral efficacious bronchodilator with the same spectrum of activity as epinephrine. In 1940, Konzett, *Arch. Exp. Path. Pharmak.*, 197, 27 (1940), outlined the effects of the potent bronchodilator isoproterenol and in 1968 Dugan, et al., *J. Pharmacol. Exp. Ther.*, 164, 290 (1968) reported the pharmacology of soterenol, a bronchodilator of greater potency, duration and oral effectiveness.

Although the aforementioned bronchodilators represent outstanding contributions toward the treatment of asthma, they all share the same undesired side effect of cardiac stimulation.

Recently, Cox and co-workers, *Adv. in Drug Res.*, 5, 115 (1970), described the pharmacology of disodium cromoglycate, an agent useful in the treatment of bronchial asthma. Although this compound is unrelated to the sympathomimetic amine bronchodilators previously mentioned, and mediates its bronchodilator effects by a unique mechanism of action, it suffers from the lack of oral efficacy.

Netherlands patent application 7008625 describes the preparation of a wide variety of pyrimidines and pyrazines including 2-aryl-4-hydroxy-5-carboxypyrimidines, claiming utility as antipyretic, analgesic, diuretic, hypoglycemic, antifibrinolytic and antiinflammatory agents.

Mitter, et al., *Quart. J. Indian Chem. Soc.*, 2, 61 (1925), has reported the synthesis of 2-phenyl-, 2-tolyl- and 2-anisyl-4-hydroxy-5-carboxypyrimidines, while the 2-phenyl congener is reported by McCarthy, et al., *J. Med. Chem.*, 7, 68 (1964). No utility was disclosed for these analogs.

SUMMARY OF THE INVENTION

The antiallergy agents of the present invention are represented by the formulae:

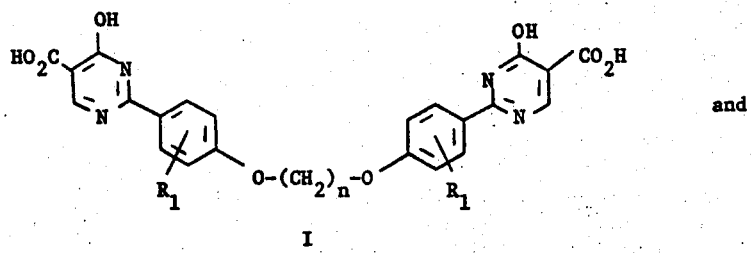

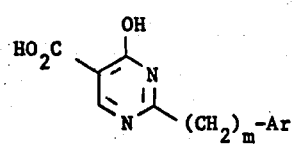

and the pharmaceutically acceptable basic salts thereof, wherein $R_1$ is hydrogen, bromo, chloro, fluoro or methoxy; $n$ is an integer of 1 to 3; Ar is pyridyl, thienyl, furyl, phenyl or phenyl substituted by hydroxy, methyl, methoxy, nitro, chloro, fluoro, 3,3-dimethoxy, 3,4,5-trimethoxy or alkanoylamino containing from 2 to 3 carbon atoms; and $m$ is an integer of 0 or 1.

The preferred compounds of formula I are those wherein $R_1$ is hydrogen and $n$ is an integer of 1 or 2, while the preferred compounds of formula II are those where Ar is pyridyl, phenyl or substituted phenyl wherein the substituent is methoxy or chloro and $m$ is 0, and where $m$ is 1 and Ar is methoxyphenyl.

In addition to their usefulness as agents in the treatment of allergic asthma, many of the compounds of the present invention manifest this activity following oral administration.

DETAILED DESCRIPTION OF THE INVENTION

In accordance with the process employed for the preparation of the 5 carboxypyrimidine derivatives of the present invention of formula I, the following scheme is illustrative:

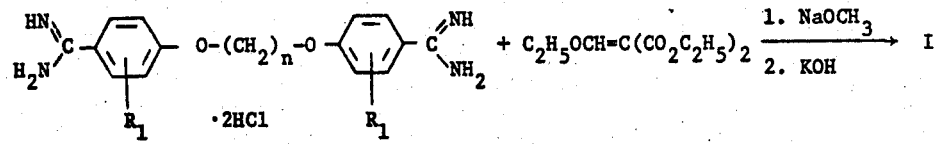

In practice, the amidine hydrochloride, wherein n and R₁ are as previously indicated, is contacted with diethyl ethoxymethylenemalonate, a commercial reagent, in a suitable inert solvent.

Such a reaction-inert solvent comprising the liquid phase of said reaction should be one which does not react to any appreciable extent with either the reactants or products of said reaction. The preferred solvents include (lower)alkanols, acetonitrile, tetrahydrofuran and N,N-di(lower)alkyl-(lower)alkylamides. The especially preferred solvent is ethanol.

At least two moles of the malonate per mole of the amidine should be employed, and at least two moles of a suitable base, usually sodium methoxide or ethoxide, plus as much as a 10–20% excess are used.

The described reaction is best carried out at elevated temperatures, preferably the reflux temperature of the reaction solvent. Under these conditions, the reaction time may vary from 12 to 36 hours.

The intermediate ester is conveniently isolated by filtration of the cooler reaction mixture followed by suspension of the solid in an aqueous medium to which sufficient acid has been added to provide a pH 1–2.

The intermediate product resulting from the above described reaction is converted to the final product or a basic salt thereof by hydrolysis of the ester moiety under basic conditions.

Experimentally, said ester is heated with an excess of an alkali metal hydroxide, e.g., potassium hydroxide, in ethanol or methanol to which has been added a moderate amount of water. The reaction generally requires several hours at the reflux temperature at which time additional alcohol is added to aid in the precipitation of the potassium salt. The salt may be utilized as the antiallergy agent or, alternately, can be converted to the free acid or a different salt.

The starting materials leading to the synthesis of the compounds of formula I are either commercial reagents or are readily prepared by methods familiar to one skilled in the art. For example, the requisite amidines are synthesized by the method of Berg, et al., *J. Chem. Soc.*, 642 (1949), while the 4-hydroxybenzonitriles employed for their synthesis are readily available through procedures described in the literature.

Compounds of formula II are prepared in a similar manner to those of formula I and comprises condensation of an aryl- or arylmethylamidine with diethyl ethoxymethylenemalonate and is previously described by Todd et al., *J. Chem. Soc.*, 364 (1937).

The appropriate amidine starting materials leading to the preparation of compounds II are synthesized by methods well known in the art, for example, those outlined by Wagner and Zook, "Synthetic Organic Chemistry," John Wiley & Sons, Inc., New York, 1953, page 634.

Hydrolysis of the intermediate ester to the corresponding acid or salts thereof is effected in a manner similar to that for the compounds of formula I. The salts, however, are generally more soluble and it is therefore preferred that the hydrolysis mixture be cooled and acidified without isolation of the basic salt.

As has been previously noted, a characteristic feature of the acidic compounds I and II of the instant invention is their ability to form basic salts. Acid congeners of the present invention are converted to basic salts by the interaction of said acid with an appropriate base in an aqueous or non-aqueous medium. Such basic reagents suitably employed in the preparation of said salts can vary in nature, and are meant to contemplate such bases as organic amines, ammonia, alkali metal hydroxides, carbonates, bicarbonates, hydrides and alkoxides, as well as alkali earth metal hydroxides, hydrides, alkoxides and carbonates. Representative of such bases are ammonia, primary amines such as n-propylamine, n-butylamine, aniline, cyclohexylamine, benzylamine, p-toluidine, ethylamine, octylamine, tertiary amines such as diethylaniline, N-methylpyrrolidine, N-methylmorpholine and 1,5-diazabicyclo[4,3,0]-5-nonene; sodium hydroxide, potassium hydroxide, ammonium hydroxide, sodium ethoxide, potassium methoxide, magnesium hydroxide, calcium hydride and barium hydroxide.

In a similar manner, treatment of the basic salts with an aqueous acid solution, e.g., mono-, di- or tribasic acid results in the regeneration of the free acid form. Such conversions are best carried out as rapidly as possible and under temperature conditions and method dictated by the stability of said acid products. The acids thus generated can be reconverted to the same or a different basic salt.

In the utilization of the chemotherapeutic activity of those compounds of the present invention which form basic salts, it is preferred, of course, to use pharmaceutically acceptable salts. Although water-insolubility, high toxicity, or lack of crystalline nature may make some salt species unsuitable or less desirable for use as such in a given pharmaceutical application, the water insoluble or toxic salts can be converted to the corresponding acids by decomposition of the salts as described above, or alternately they can be converted to any desired pharmaceutically acceptable basic salt. The said pharmaceutically acceptable salts preferred are those wherein the cation is ammonium, sodium or potassium.

As previously noted, 5-carboxypyrimidines of the present invention are all readily adapted to therapeutic use in preventing allergic symptoms in mammalian subjects by administering to said subject an effective amount of a compound of formulae I or II. Especially of interest is the alleviation of the symptoms of allergic asthma. Compounds notable for this therapeutic use include bis(4-[4'-hydroxy-5'-carboxy-2'-pyrimidinyl]phenoxy)methane, 1,2-bis(4-[4'-hydroxy-5'-carboxy-2'-pyrimidinyl]phenoxy)ethane, 2-phenyl-4-hydroxy-5-carboxypyrimidine, 2-(p-methoxyphenyl)-4-hydroxy-5-carboxypyrimidine, 2-(p-chlorophenyl)-4-hydroxy-5-carboxypyrimidine, 2-(3'-pyridyl)-4-hydroxy-5-carboxypyrimidine, 2-(4'-pyridyl)-4-hydroxy-5-carboxypyrimidine and 2-(p-methoxybenzyl)-4-hydroxy-5-carboxypyrimidine.

The 5-carboxypyrimidines and the pharmaceutically acceptable basic salts thereof, which are useful antiallergy agents in mammals may be administered either as individual therapeutic agents or as mixtures of therapeutic agents. They may be administered alone, but are generally administered with a pharmaceutical carrier selected on the basis of the chosen route of administration and standard pharmaceutical practice. For example, they may be combined with various pharmaceutically acceptable inert carriers in the form of tablets, capsules, lozenges, troches, hard candies, powders, aerosol sprays, aqueous suspensions or solutions, injectable solutions, elixirs, syrups and the like. Such carriers include solid diluents, or filters, sterile aqueous media and various nontoxic organic solvents. Moreover, the oral pharmaceutical compositions of this invention may be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of the standard pharmaceutical practice. For example, where those compounds are administered orally, those compounds of formula II, in tablet form, excipients such as lactose, sodium citrate, calcium carbonate and dicalcium phosphate may be used. Various disintegrants such as starch, alginic acids, and certain comples silicates, together with lubricating agents such as magnesium stearate, sodium lauryl sulphate and talc, may also be used in producing tablets for the oral administration of these compounds. For oral administration in capsule form, lactose and high molecular weight polyethylene glycols are among the preferred materials for use as pharmaceutically acceptable carriers. Where aqueous suspensions are to be used for oral administration, the compounds of this invention may be combined with emulsifying or suspending agents. Diluents such as ethanol, propylene glycol, glycerine and their combinations may be employed as well as other materials.

For the purpose of parenteral administration and inhalation, solutions or suspensions of the instant compounds of formulae I and II in sesame or peanut oil or in aqueous propylene glycol solutions can be employed, as well as sterile aqueous solutions of the solution acid addition salts described hereinafter. These particular solutions are especially suited for intramuscular and subcutaneous injection purposes. The aqueous solutions, including those of the acid addition salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

The compounds may be administered to asthmatic subjects suffering from bronchoconstriction by means of inhalators or other devices which permit the active compounds to come into direct contact with the constricted areas of the tissues of the subject. When administeed by means of a spray formulated as a 1% solution in an aqueous or nonaqueous solvent, e.g., freons, utilization several times a day is preferred.

It is necessary that the active ingredient form a proportion of the composition such that a suitable dosage form will be obtained. Obviously, several dosage unit forms may be administered at about the same time. Although compositions with less than 0.005% by weight of active ingredient might be used in certain instances, it is preferred to use compositions containing not less than 0.005% of the active ingredient; otherwise the amount of carrier becomes excessively large. Activity increases with the concentration of the active ingredient. The composition may contain 10, 50, 75, 95 or an even higher percentage by weight of the active ingredient.

Regarding the test procedure employed to evaluate the compounds of the present invention, it has been found that the Passive Cutaneous Anaphylaxis (PCA) reaction demonstrates an excellent correlation between activity for compounds in this test and their utility in the treatment of alleric asthma. The ability of agents to interfere with PCA reactions is measured in male Charles River Wistar rats, 170–210 g. Reaginic antisera is prepared according to Mota, *Immunology*, 7, 681 (1964), using hen egg albumin and *B. pertussis*. Hyperimmune antisera to hen egg albumin is prepared according to Orange, et al, *J. Exptl. Med.*, 127, 767 (1968). Forty-eight hours prior to antigen challenge the reaginic antisera is injected intradermally into the shaved skin of a normal rat's back; 5 hours before challenge the hyperimmune antisera is similarly injected; 5 hours later, at a third site, 60 mcg histamine dihydrochloride is injected i.d. as a check for antihistaminic and unspecified types of blockade; the compounds of the instant invention or saline are then administered i.v. or orally immediately followed by 2.5 mg. Evan's blue dye and 5 mg. egg albumin in saline. Thirty minutes later the animals were asphyxiated using chloroform and the skin of the back removed and reversed for observation. A score is assigned each injection site equal to the product of the diameter of the site in mm. and a grade of 0.1, 0.5, 1, 2, 3 or 4 proportional to intensity of dye coloration. The scores for a given injection site are summed for each group of 8 animals and compared to the saline treated controls. The difference is expressed as percent blockade due to the compound employed.

Compounds representative of those in the present invention are tested by the aforementioned procedure, and the resulting activities are reported as the % protected animals. Disodium Cromoglycate, a commercial antiallergy agent, is included for comparison.

% Protected in PCA Screen

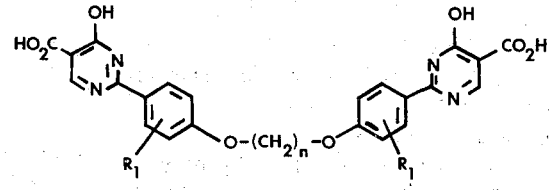

| | | DOSE | | | |
|---|---|---|---|---|---|
| | | 1 mg./kg. I.V. | 10 mg./kg. I.V. | 30 mg./kg. ORAL | 100 mg./kg. ORAL |
| R₁ | n | | | | |
| H | 1 | — | 29 | 0 | 0 |
| H | 2 | 50 | 98 | 0 | 0 |

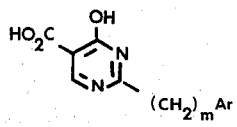

| Ar | m | Dose | | | |
|---|---|---|---|---|---|
| | | 1 mg./kg. I.V. | 10 mg./kg. I.V. | 30 mg./kg. ORAL | 100 mg./kg. ORAL |
| $C_6H_5-$ | 0 | 42 | 96 | — | 0 |
| $p-CH_3C_6H_4-$ | 0 | 50 | — | — | — |
| $m-CH_3C_6H_4-$ | 0 | 25 | — | — | — |
| $p-ClC_6H_4-$ | 0 | — | 57 | — | — |
| $m-NO_2C_6H_4-$ | 0 | 43 | 86 | — | 20 |
| $p-CH_3OC_6H_4-$ | 0 | 57 | 100 | 20 | 91 |
| $p-HOC_6H_4-$ | 0 | 50 | — | — | — |
| $3,4-(CH_3O)_2C_6H_3-$ | 0 | 33 | — | — | — |
| $3,4,5-(CH_3O)_3C_6H_2-$ | 0 | 50 | — | — | — |
| $p-CH_3OC_6H_4-$ | 1 | — | 60 | — | — |
| $3,4-(CH_3O)_2H_3-$ | 1 | 17 | — | — | — |
| 2-pyridyl | 0 | — | 30 | — | — |
| 3-pyridyl | 0 | 50 | 100 | — | 27 |
| 4-pyridyl | 0 | 14 | 86 | — | 36 |
| Disodium chromoglycate | 63 | — | 0 | 0 | |

Regarding utility, and in particular the dosage regimen, obviously the physican will ultimately determine the dosage which will be most suitable for a particular individual, and it will vary with age, weight and response of the particular patient as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by asmall quantity administered parenterally.

Having full regard for the foregoing factors, it is considered that an effective daily dosage of the compounds of the present invention in humans of approximately 20 to 200 mg. per day, with a preferred range of about 75 to 180 mg. per day in single or divided doses, or at about 1 to 3 mg./kg. of body weight will effectively alleviate bronchoconstriction in human subjects. These values are illustrative, and there may, of course, be individual cases where higher or lower dose ranges are merited.

The following examples are provided solely for the purpose of illustration and are not to be construed as limitations of this invention, many variations of which are possible without departing from the spirit or scope thereof.

EXAMPLE 1

Bis(4-[4'hydroxy5'-carboxy-2'-pyrimidinyl]phenoxy)methane I; $R_1 = H$ and $n = 1$)

A. Bis(4-cyanophenoxy)methane

To a suspension of 48 g. (0.4 mole) of 4hydroxybenzonitrile in 200 ml. of ethanol is added portion-wise 200 ml. of ethanol containing 9.2 g. of reacted sodium metal, followed by the dropwise addition of 53.4 g. (0.2 mole) of methylene iodide. The reaction mixture is heated to reflux overnight, cooled and filtered. The first crop of crude product consists of 2.0 g., m.p. 130°–138°C., while the second crop, obtained by concentration of the filtrate to one-third volume, is 10.2 g., m.p. 137°–142°C. The crops are combined and recrystallized from acetic acid, 9.8 g., m.p. 145° C.

B. Bis(4-guanylphenoxy)methane dihydrochloride

Into a slurry of 9.8 g. (0.039 mole) of bis(4-cyanophenoxy)methane in 20 ml. of chloroform containing 7 ml. of ethanol is bubbled hydrogen chloride gas until 3.3 g. has been absorbed, and the resulting homogenous solution allowed to stand at room temperature for two days. The resulting suspension is stirred while 170 ml. of an 8 % ammonia in ethanol solution is added. After stirring for several hours, the mixture is again allowed to stand for two days. The insolubles are filtered, ether added to the filtrate, and the precipitated product is collected by filtration and dried, 8.4 g., m.p. 225° C. dec.

C. Bis(4-[4'-hydroxy-5'-carbethoxy-2'-pyrimidinyl]-phenoxy]methane

A suspension of 8.0 g. (22 m moles) of bis(4-guanylphenoxy)methane dihydrochloride in 250 ml. of ethanol, under a nitrogen atmosphere is treated with 9.5 g. (44 m moles) of diethyl ethoxymethylenemalonate followed by 2.6 g. (48 m moles) of sodium methoxide. After refluxing for 18 hrs. the mixture is filtered and the filtrate diluted with 250 ml. of water. The pH of the aqueous mixture is adjusted to ~1.0 by the addition of 12N hydrochloric acid and the precipitate is filtered and dried, 6.4 g., m.p. 280° C. dec.

D. Bis(4-[4'-hydroxy-5'-carboxy-2'-pyrimidinyl]-phenoxy)methane and dipotassium Salt Two and seven-tenths grams (5 m moles) of the above ester is added to 100 m. of ethanol containing 50 ml. of water and 1.7 g. of potassium hydroxide, and the solution heated to reflux for 18 hrs. Additional ethanol is added to precipitate the dipotassium salt as the tetrahydrate, 1.6 g.

Anal. Calc'd for $C_{23}H_{14}O_8N_4K_2·4H_2O$: C, 39.4; H, 2.9; N, 8.0. Found: C, 39.5; H, 2.7; N, 7.9.

The free acid is obtained by treating an aqueous solution of the dipotassium salt with sufficient 6N hydrochloric acid to provide a pH of 1–2 followed by filtration and drying of the precipitated product.

EXAMPLE 2

1,2-Bis(4'[4'-hydroxy-5'-carboxy-2'-pyrimidinyl]-phenoxy)ethane I; $R_1 = H$ and $n = 2$)

A. 1,2-Bis(4-cyanophenoxy)ethane

A solution of 200 ml. of ethanol containing 9.2 g. (0.4 mole) of reacted sodium metal is added to a suspension of 48 g (0.4 mole) of 4-hydroxybenzonitrile, followed by 37.2 g. (0.2 mole) of 1,2-dibromoethane, and the resulting mixture heated to reflux for 18 hrs. An additional 18.9 g. (0.1 mole) of the dibromide is added and heating continued for 18 hrs. Finally, 9.5 g. (0.5 mole) more of the dibromide is added and heating continued for 4 hrs. The reaction mixture is cooled and the precipitate, which consists of potassium bromide and the desired intermediate, is subsequently slurried in water and filtered, 30 g., m.p. 196°–197° C.

1,2-Bis(4-guanylphenoxy)ethane dihydrochloride

Hydrogen chloride gas is bubbled into a suspension of 26.0 g. (0.1 mole) of 1,2-bis(4-cyanophenoxy)ethane in 25 ml. of chloroform containing 12 ml. of ethanol until 7.3 g. has been absorbed. After the suspension has remained at room temperature for two days, it is treated with 90 ml. of an 8% ammonia in ethanol solution, and allowed to stir for an additional two days. The solids are filtered and extracted with 500 ml. of hot water, and the aqueous solution concentrated to 100 ml. The precipitate which crystallizes from the cooled, concentrated aqueous extract is filtered and dried, 6.0 g., m.p. 320° C. dec.

C. 1,2-Bis(4'-[4'-hydroxy-5'-carbethoxy-2'-pyrimidinyl]phenoxy)ethane

To a suspension of 5.6 g. (15 m moles) of the above guanyl compound in 60 ml. of ethanol and maintained under a nitrogen atmosphere is added 6.5 g. 30 m moles) of diethyl ethoxymethylenemalonate and 1.6 g. (30 m moles) of sodium methoxide, and the suspension stirred at room temperature overnight and then at 45°C. for 18 hrs. An additional 1.6 g. of sodium methoxide is added and heating at 75°C. continued for 18 hrs.

The solids are filtered, suspended in water and the aqueous phase is separated and acidified with 12N hydrochloric acid to pH 1.0. The resulting precipitate is filtered and dried, 5.6 g., m.p. 310° C. dec.

D. 1,2-Bis(4-[4'-hydroxy-5'-carboxy-2'-pyrimidinyl]phenoxy)ethane and dipotassium salt A solution of 4.0 g. (7.4 m moles) of the above ester in 150 ml. of ethanol containing 80 ml. of water and 2.7 g. of potassium hydroxide is heated to reflux under an atmosphere of nitrogen. After 16 hrs. the solution is cooled in an ice bath, diluted with additional ethanol, and the crystallized salt filtered and dried, 2.3 g., m.p. >300°C.

The free acid is obtained by acidification of an aqueous solution of the above salt with 6N hydrochloric acid.

EXAMPLE 3

1,3-Bis(4-[4'-hydroxy-5'-carboxy-2'-primidinyl]-phenoxy)propane I; $R_1 = H$ and $n = 3$)

A. 1,3-Bis(4-cyanophenoxy)propane

In a manner similar to the procedures of Examples 1A and 2A, 48.0 g. (0.4 mole) of 4-hydroxybenzonitrile, 9.2 g. (0.4 mole) of sodium metal and 40.0 g. (0.2 mole) of 1,3-dibromopropane provided 41.5 g. of the desired intermediate, m.p. 186–187° C.

B. 1,3-Bis(4-guanylphenoxy)propane dihydrochloride

Hydrogen chloride gas is bubbled into a suspension of 41.0 g. (0.147 mole) of the above cyano compound in 100 ml. of chloroform and 20 g. of ethanol until the theoretical amount has been added, 10.8 g. After remaining at room temperature for 3 days, additional hydrogen chloride is added over a period of 30 min. and the mixture allowed to remain at room temperature for one week.

The solids are filtered, and ether added to the filtrate. The precipitate which slowly crystallizes is filtered and dried, 4.5 g.

C. 1,3-Bis(4-[4'-hydroxy-5'-carbethoxy-2'-pyrimidinyl]phenoxy)propane

In a manner similar to the procedures of Examples 1C and 2C, the desired intermediate is obtained by the reaction of 3.85 g. (0.01 mole) of 1,3-bis(4-guanyl-phenoxy)propane, 4.32 g. (0.02 mole) of diethyl ethoxymethylenemalonate and 1.1 g. (0.02 mole) of sodium methoxide in 50 ml. of ethanol.

D. 1,3-Bis(4-[4'-hydroxy-5'-carboxy-2'-pyrimidinyl]phenoxy)propane and dipotassium salt A mixture of 2.8 g. (5 m moles) of 1,3-bis(4-[4'-hydroxy-5'-carbethoxy-2'-pyrimidinyl]phenoxy)propane and 1.7 g. of potassium hydroxide in 100 ml. of ethanol containing 50 ml. of water is heated to reflux overnight. The solution is cooled, diluted with 100 ml. of ethanol and the crystallized potassium salt filtered and dried.

The free acid is obtained by adjusting the pH of an aqueous solution of the above salt to 1, followed by filtration and drying of the precipitated solids.

EXAMPLE 4

Following the procedures of Examples 1, 2 or 3, and employing the requisite starting chemical reagents, the bis(phenoxy)alkanes listed below are synthesized.

| n | $R_1$ | n | $R_1$ |
|---|---|---|---|
| 1 | 2-F | 1 | 2-$CH_3O$ |
| 3 | 2-F | 2 | 2-$CH_3O$ |
| 1 | 2-Cl | 3 | 2-$CH_3O$ |
| 2 | 2-Cl | 2 | 3-$CH_3O$ |
| 3 | 2-Cl | 2 | 2-$CH_3$ |
| 2 | 3-Cl | 3 | 2-$CH_3$ |

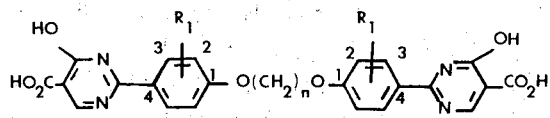

| n | R₁   | n | R₁    |
|---|------|---|-------|
| 1 | 2-Br | 1 | 3-CH₃ |
| 3 | 2-Br | 2 | 3-CH₃ |
| 3 | 3-Br | 3 | 3-CH₃ |

EXAMPLE 5

2-Phenyl-4-hydroxy-5-carboxypyrimidine (II; Ar = $C_6H_5$ and $m = 0$)

To a solution of ethanol containing 1.32 g. (0.058 mole) of reacted sodium metal is added 12.4 g. (0.058 mole) of diethyl ethoxymethylenemalonate followed by 10.0 g. (0.058 mole) of benzamidine hydrochloride hydrate, and the mixture heated to reflux overnight. The reaction mixture is cooled and filtered and the filtrate concentrated to an oil which on addition to 200 ml. of water and acidification precipitates a white solid. The intermediate ester is filtered and dried, 9.0 g., m.p. 209–210° C. A small sample is recrystallized from methanol, m.p. 210°–211° C.

Three grams (12 m moles) of the above ester is heated in 75 ml. of ethanol containing 1.34 g. of potassium hydroxide to the reflux temperature for 5 hrs. The mixture is cooled, filtered and the filtrate diluted with 50 ml. of water and acidified to pH 1 to 6N hydrochloric acid. The crystallized product is filtered and dried, 2.0 g., m.p. 274° C. dec.

Anal. Calc'd for $C_{11}H_8O_3N_2$: C, 61.1; H, 3.7; N, 13.0. Found: C, 60.7; H, 3.9; N, 13.0.

EXAMPLE 6

2-(m-Tolyl)-4-hydroxy-5-carboxypyrimidine (II; Ar = m-$CH_3C_6H_4$ and $m = 0$)

To a suspension of 17.0 g. (0.1 mole) of m-toluamidine hydrochloride in 200 ml. of ethanol and under a nitrogen atmosphere is added successively 21.6 g. (0.11 mole) of diethyl ethoxymethylenemalonate and 5.9 g. (0.11 mole) of sodium methoxide. After heating the reaction mixture to reflux for several hours, it is cooled and filtered. The filtered solids are dissolved in water and treated with sufficient 12N hydrochloric acid to provide a pH 1. The precipitated solids are filtered and dried, 10.2 g., m.p. 160°–161° C.

A solution of 5.16 g. of the above ester intermediate in 200 ml. of ethanol containing 2.24 g. of potassium hydroxide is heated to reflux for 2.5 hrs. The solution is cooled and acidified with 12N hydochloric acid, and the precipitated solid filtered and dried, 4.4 g., m.p. 278° C. dec.

EXAMPLE 7

2-(p-Tolyl)-4-hydroxy-5-carboxypyrimidine (II; Ar = p-$CH_3C_6H_4$ and $m = 0$)

In a manner similar to the procedure of Example 6, 11.9 g. (0.07 mole) of p-toluamidine hydrochloride, 15.12 g. (0.07 mole) of diethyl ethoxymethylenemalonate and 4.2 g. (0.077 mole) of sodium methoxide in 150 ml. of ethanol, after refluxing overnight, provided 9.2 g. of 2-(p-toly)-4-hydroxy-5-carbethoxypyrimidine.

Hydrolysis of 5.16 g. (0.02 mole) of the above ester with 2.24 g. of potassium hydroxide in 200 ml. of ethanol at reflux temperatures gave 4.5 g. of the desired product, m.p. 285° C. dec.

EXAMPLE 8

2-(p-Anisyl)-4-hydroxy-5-carboxypyrimidine (II; Ar = p-$CH_3OC_6H_4$ and $m = 0$)

An ethanol (100 ml.) suspension of 10.0 g. (0.062 mole) of p-anisamidine hydrochloride, 13.4 g. (0.062 mole) diethyl ethoxymethylenemalonate and 3.68 g. (0.068 mole) of sodium methoxide is heated to reflux overnight. The solids from the filtered solution are suspended in water and acidified with 6N hydrochloric acid to give 9.9 g. of the ester intermediate, m.p. 224°–226° C.

Treatment of 4.5 g. of the above intermediate with 2.0 g. of potassium hydroxide in 200 ml. of ethanol and 50 ml. of water at reflux temperatures gave, on acidification of the cooled reaction solution, 4.3 g. of the desired product, m.p. 274° C. dec.

EXAMPLE 9

2-(p-Methoxybenzyl)-4-hydroxy-5-carboxypyrimidine (II; Ar = p-$CH_3OC_6H_4$ and $m = 1$)

A reaction mixture comprising 10 g. (0.05 mole) of p-methoxyphenylacetamidine hydrochloride, 10.8 g. (0.05 mole) of diethyl ethoxymethylenemalonate and 3.0 g. (0.055 mole) of sodium methoxide in 100 ml. of ethanol is heated to reflux overnight. The mixture is filtered and the filtrate concentrated in vacuo to a yellow oil, which on trituration with 150 ml. of water at pH 1 solidifies, 8.0 g., m.p. 107°–111° C. Recrystallization from ethyl acetate gave 5.4 g., m.p. 147°–149° C.

Hydrolysis of 2.88 g. of the above ester with 1.12 g. of potassium hydroxide in 150 ml. of ethanol and 30 ml. of water gave, on acidification to pH 1 of the concentrated reaction mixture, 1.85 g. of the desired product as the hydrochloride salt. Conversion to the amphoteric product is carried out by back-adjusting an aqueous solution of the acid addition salt with a 1N sodium hydroxide solution to pH 2.

EXAMPLE 10

Employing the procedure of Examples 5 through 9, and starting with the appropriate aryl- or arylmethylamidine, the following congeners are prepared: 2-Benzyl-4-hydroxy-5-carboxypyrimidine, 2-(o-tolyl)-4-hydroxy-5-carboxypyrimidine, 2-(o-methylbenzyl)-4-hydroxy-5-carboxypyrimidine, 2-(p-methylbenzyl)-4-hydroxy-5-carboxypyrimidine, 2-(o-methoxybenzyl)-

4-(hydroxy-5-carboxypyrimidine, 2-(m-anisyl)-4-hydroxy-5-carboxypyrimidine and 2-(o-anisyl)-4-hydroxy-5-carboxypyrimidine.

EXAMPLE 11

2-(p-Chlorophenyl)-4-hydroxy-5-carboxypyrimidine (II; Ar = p-ClC$_6$H$_4$ and m = O)

Sodium methoxide (3.14 g.; 0.05 mole) is added to a suspension of 10.0 g. (0.052 mole) of p-chlorobenzamidine hydrochloride and 11.4 g. (0.052 mole) of diethyl ethoxymethylenemalonate in 100 ml. of ethanol, and the resulting reaction mixture heated to reflux overnight. The mixture is cooled and the precipitated solid slurried in water rendered acid to pH 1.0 with 6N hydrochloric acid. The ester intermediate is filtered and dried, 7.4 g., m.p. 231°–233° C.

By previously described hydrolysis procedures, 4.18 g. (15 m moles) of the above ester and 1.68 g. (30 m moles) of potassium hydroxide in 180 ml. of ethanol and 35 ml. of water yield, after 3.0 hrs. at reflux and work-up, 4.3 g. of product, m.p. 312° C. dec.

EXAMPLE 12

Employing the procedures of Examples 5 through 9 and 11, and starting with the requisite amidine, the following analogs are synthesized:

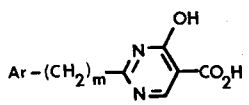

| Ar | m | Ar | m |
|---|---|---|---|
| o-ClC$_6$H$_4$— | 0 | o-FC$_6$H$_4$— | n |
| m-ClC$_6$H$_4$— | 0 | m-FC$_6$H$_4$— | 0 |
| m-ClC$_6$H$_4$— | 1 | m-FC$_6$H$_4$— | 1 |
| p-ClC$_6$H$_4$— | 1 | p-FC$_6$H$_4$— | 0 |
| o-ClC$_6$H$_4$— | 1 | p-FC$_6$H$_4$— | 1 |

EXAMPLE 13

2-(m-Nitrophenyl)-4-hydroxy-5-carboxypyrimidine (II; Ar = m-NO$_2$C$_6$H$_4$ and m = O)

A mixture of 27.0 g. (0.135 mole) of m-nitrobenzamidine hydrochloride, 29.2 g. (0.135 mole) of diethyl ethoxymethylenemalonate and 8.0 g. (0.148 mole) of sodium methoxide in 190 ml. of ethanol is heated to reflux overnight, and is then cooled in an ice bath. The precipitated solid is filtered, suspended in 350 ml. of water and treated with sufficient 6N hydrochloric acid to provide a pH of 1.5. The intermediate ester is filtered and recrystallized from methanol, 8.0 g., m.p. 184°–187° C.

The above ester (4.34 g., 15 m moles) is hydrolyzed to the desired acid by the aforementioned procedure, employing 1.68 g. (30 m moles) of potassium hydroxide in 180 ml. of ethanol and 35 ml. of water and a reflux time 6.5 hrs., to yield 3.1 g., m.p. 288° C. dec.

EXAMPLE 14

The procedure of Example 13 is repeated, starting with the appropriate amidines, to provide the following congeners:

2-(o-Nitrophenyl)-4-hydroxy-5-carboxypyrimidine, 2-(o-nitrobenzyl)-4-hydroxy-5-carboxypyrimidine, 2-(m-nitrobenzyl)-4-hydroxy-5-carboxypyrimidine, 2-(p-nitrophenyl)-4-hydroxy-5-carboxypyrimidine and 2-(p-nitrobenzyl-4-hydroxy-5-carboxypyrimidine.

EXAMPLE 15

2-(3,4-Dimethoxyphenyl)-4-hydroxy-5-carboxypyrimidine (II; Ar = 3,4-(CH$_3$O)$_2$C$_6$H$_3$ and m = O)

After heating a mixture of 8.0 g. (37 m moles) of 3,4-dimethoxybenzamidine hydrochloride, 8.0 g. (37 m moles) of diethyl ethoxymethylenemalonate and 2.16 g. (40 m moles) of sodium methoxide in 175 ml. of ethanol at reflux temperature overnight, the resulting solids are filtered and suspended in water. The pH of the suspension is adjusted to approximately 1.0 using 6N hydrochloric acid and the precipitate filtered and dried, 4.1 g., m.p. 225°–227° C.

The above intermediate ester is hydrolyzed by heating 3.04 g (10 m moles) with 1.1 g. (20 m moles) of potassium hydroxide in 100 ml. of ethanol and 25 ml. of water to yield 2.54 g. of product, m.p. 278°C. dec.

In a similar manner are prepared: 2-(3,4-Dimethoxybenzyl)-4-hydroxy-5-carboxypyrimidine (II; Ar = 3,4-(CH$_3$O)C$_6$H$_3$ and m = 1), m.p. 185° C. dec. and 2-(3,4,5,-trimethoxyphenyl)-4-hydroxy-5-carboxypyrimidine (II; Ar = 3,4,5-(CH$_3$O)$_3$C$_6$H$_2$ and m = 0), m.p. 234° C. dec.

EXAMPLE 16

2-(p-Hydroxyphenyl)-4-hydroxy-5-carboxypyrimidine (II; Ar = p-HOC$_6$H$_4$ and m = 0)

In a manner similar to previous examples, 6.0 g. (35 m moles) of p-hydroxybenzamidine, 7.6 g. (35 m moles) of diethyl ethoxymethylenemalonate and 2.1 g. (39 m moles) of sodium methoxide gives 7.3 g. of the ester intermediate 3.9 g. of which is converted on hydrolysis to 1.7 g. of the desired product, m.p. 310° C. dec.

Similarly are prepared 2-(m-hydroxyphenyl)-4-hydroxy-5-carboxypyrimidine, 2-(o-hydroxybenzyl)-4-hydroxy-5-carboxypyrimidine and 2-(p-hydroxybenzyl)-4-hydroxy-5-carboxypyrimidine.

EXAMPLE 17

2-(m-Acetamidophenyl)-4-hydroxy-5-carboxypyrimidine (II; Ar = p-CH$_3$CONHC$_6$H$_4$ and m = 0)

A suspension of 2.89 g. (0.01 mole) of 2-(m-nitrophenyl)-4-hydroxy-5-carbethoxypyrimidine, prepared in Example 13, and 350 mg. of platinum oxide in 200 ml. of methanol is shaken in an atomsphere of hydrogen at an initial pressure of 45 p.s.i. When the theoretical amount of hydrogen has been absorbed, the catalyst is filtered and the filtrate concentrated in vacuo.

The crude residual 2-(m-aminophenyl)-4-hydroxy-5-carbethoxypyrimidine is heated for 4.5 hrs. in 150 ml. of ethanol containing 1.12 g. (0.02 mole) of potassium hydroxide and 25 ml. of water. The mixture is concentrated under reduced pressure to a small volume and sufficient 6N hydrochloric acid added such that the aqueous phase is just acid to Congo red paper. The resulting solid, 2-(m-aminophenyl-4-hydroxy-5-carboxypyrimidine, is filtered and dried.

Without further purification, 1.65 g. (5 m moles) of 2-(m-aminophenyl)-4-hydroxy-5-carboxypyrimidine in 25 ml. of ethyl acetate, to which is added 1.1 g. of acetic anhydride, is heated to reflux for 3 hrs. The reaction mixture is subsequently cooled in an ice bath, and the precipitated product filtered, dried and recrystallized from a large volume of methanol.

EXAMPLE 18

Starting with the appropriate 2-(nitrophenyl-4-hydroxy-5-carbethoxypyrimidine esters prepared in Examples 13 and 14 and requisite alkanoic anhydrides, and repeating the procedure of Example 17, the following analogs are prepared:

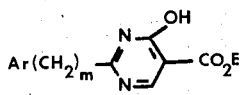

| Ar | m | Ar | m |
|---|---|---|---|
| m-CH₃CH₂CONHC₆H₄— | 0 | p-CH₃CONHC₆H₄— | 0 |
| o-CH₃CONHC₆H₄— | 0 | p-CH₃CH₂CONHC₆H₄— | 0 |
| o-CH₆CONHC₆H₄— | 1 | p-CH₃CONHC₆H₄— | 1 |
| o-CH₃CH₂CONHC₆H₄— | 1 | p-CH₃CH₂CONHC₆H₄— | 1 |

EXAMPLE 19

2-(4'-Pyridyl)-4-hydroxy-5-carboxypyrimidine (II; Ar = 4-pyridyl and m = 0)

A mixture of 41.8 g. (0.25 mole) of 4-guanylpyridine hydrochloride, 54.0 g. (0.25 mole) of diethyl ethoxymethylenemalonate and 14.9 g. (0.275 mole) of sodium methoxide in 200 ml. of methanol is heated to reflux for 21 hrs. The suspended solids are filtered and the filtrate concentrated to an oil under reduced pressure. Water is added to the residual oil and the solids remaining out of solution are filtered, 3.2 g., m.p. 195°–198° C. The aqueous filtrate is extracted at pH 10 with chloroform and then adjusted to pH 4, forming additional solids, 2.2 g., m.p. 195°–198° C. The aqueous is extracted with chloroform on the acid side (pH 4) and the chloroform layer subsequently concentrated to near dryness, 700 mg., m.p. 195°–200° C.

The initially isolated crops are combined and triturated with ethanol, 5.0 g., and the product isolated from the chloroform extract recrystallized from methanol, to provide the analytical sample, 670 mg., m.p. 198°–200° C.

Anal. Calc'd for $C_{12}H_{11}O_3N_3$: C, 58.8; H, 4.5; N, 17.1. Found: C, 58.5; H, 4.5; N, 17.3.

The above intermediate ester (2.45 g.; 0.01 mole) is heated at reflux temperatures with 1.12 g. (0.02 mole) of potassium hydroxide in 120 ml. of ethanol and 25 ml. of water for 4 hrs. The solvent is removed in vacuo and the residual soft solid dissolved in 50 ml. of water. Addition of 6N hydrochloric acid to pH 4 precipitates the desired product which is filtered and dried, m.p. >320° C.

In a similar manner, starting with the appropriate reagents, are prepared:
2-(2'-Pyridyl)-4-hydroxy-5-carboxypyrimidine (II; Ar = 2-pyridyl and m = 0) m.p. 208° C. dec. and 2-(3'-pyridyl)-4-hydroxy-5-carboxypyrimidine (II; Ar = 3-pyridyl and m = 0) m.p. 310° C. dec.

EXAMPLE 20

The procedure of Example 19 is repeated, starting with the requisite amidine, to provide the following products: 2-(2'-pyridylmethyl)-4-hydroxy-5-carboxypyrimidine, 2-(4'-pyridylmethyl)-4-hydroxy-5-carboxypyrimidine, 2-(2'-thienyl)-4-hydroxy-5-carboxypyrimidine, 2-(2'-thenyl)-4-hydroxy-5-carboxypyrimidine, 2-(3'-thenyl)-4-hydroxy-5-carboxypyrimidine, 2-(2'-furfuryl)-4-hydroxy-5-carboxypyrimidine, 2-(3'-furfuryl)-4-hydroxy-5-carboxypyrimidine and 2-(2'-furyl)-4-hydroxy-5-carboxypyrimidine.

EXAMPLE 21

Tablets

A tablet base is prepared by blending the following ingredients in the proportion by weight indicated:

| Sucrose, U.S.P. | 80.3 |
|---|---|
| Tapioca Starch | 13.2 |
| Magnesium Stearate | 6.5 |

Into this tablet base there is blended sufficient 2-(p-methoxyphenyl)-4-hydroxy-5-carboxypyrimidine to provide tablets containing 20, 100 and 250 mg. of active ingredient per tablet. The compositions are each compressed into tablets, each weighing 360 mg., by conventional means.

EXAMPLE 22

Capsules

A blend is prepared containing the following ingredients:

| Calcium carbonate, U.S.P. | 17.6 |
|---|---|
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient 2-(p-methoxyphenyl)-4-hydroxy-5-carboxypyrimidine to provide capsules containing 10, 25 and 50 mg. of active ingredient per capsule. The compositions are filled into conventional hard gelatin capsules in the amount of 350 mg. per capsule.

EXAMPLE 23

Injectable Preparation

One thousand grams of 1,2-bis(4[4'-hydroxy-5'-carboxy-2'-pyrimidinyl]-phenoxy)ethane disodium salt are intimately mixed and ground with 2500 grams of sodium ascorbate. The ground dry mixture is placed in vials and sterilized with ethylene oxide after which the vials are sterilely stoppered. For intravenous administration, sufficient water is added to the materials in the vials to form a solution containing 5.0 mg. of active ingredient per milliliter of injectable solution.

EXAMPLE 24

Solution

A solution of 2-(p-methoxyphenyl)-4-hydroxy-5-carboxypyrimidine sodium salt is prepared with the following composition:

| Effective ingredient | 6.04 grams |
|---|---|
| Magnesium chloride hexahydrate | 12.36 grams |
| Monoethanolamine | 8.85 ml. |
| Propylene glycol | 376.00 grams |
| Water, distilled | 94.00 ml. |

The resultant solution has a concentration of effective ingredient of 10 mg./ml. and is suitable for parenteral and especially for intramuscular administration.

EXAMPLE 25

Suspension

A suspension of 2-(p-methoxyphenyl)-4-hydroxy-5-carboxypyrimidine is prepared with the following composition:

| | |
|---|---|
| Effective ingredient | 25.00 g. |
| 70% aqueous sorbitol | 741.29 g. |
| Glycerine, U.S.P. | 185.35 g. |
| Gum acacia (10% solution) | 100.00 ml. |
| Polyvinylpyrrolidone | 0.50 g. |
| Distilled water | Sufficient to make 1 liter |

To this suspension, various sweeteners and flavorants are added to improve the palatability of the suspension. The suspension contains approximately 25 mg. of effective agent per milliliter.

What is claimed is:

1. A method of preventing asthmatic symptoms in a human who is subject to bronchoconstriction which comprises administering to said human an asthmatic symptom preventing amount of a compound of the formula

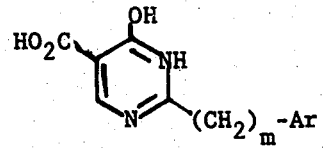

or a pharmaceutically acceptable basic salt thereof wherein Ar is furyl and $m$ is an integer of 0 to 1.

2. The method of claim 1 wherein said symptoms are the result of allergic asthma.

3. The method of claim 2 wherein Ar is 2-furyl and $m$ is 0.

* * * * *